(12) United States Patent
Zoabi

(10) Patent No.: US 9,795,801 B2
(45) Date of Patent: Oct. 24, 2017

(54) COMBINATION AROMA AND MAGNETOTHERAPY DEVICE AND METHODS OF USE

(71) Applicant: Talal Zoabi, Nazareth (IL)

(72) Inventor: Talal Zoabi, Nazareth (IL)

(*) Notice: Subject to any disclaimer, the term of this patent is extended or adjusted under 35 U.S.C. 154(b) by 405 days.

(21) Appl. No.: 14/306,924

(22) Filed: Jun. 17, 2014

(65) Prior Publication Data

US 2015/0360044 A1    Dec. 17, 2015

(51) Int. Cl.
| | |
|---|---|
| *A61N 2/00* | (2006.01) |
| *A61N 2/06* | (2006.01) |
| *A61M 11/04* | (2006.01) |
| *A61G 10/02* | (2006.01) |
| *A61M 11/00* | (2006.01) |
| *A61M 15/08* | (2006.01) |

(52) U.S. Cl.
CPC .............. *A61N 2/002* (2013.01); *A61G 10/02* (2013.01); *A61M 11/04* (2013.01); *A61N 2/06* (2013.01); *A61M 11/005* (2013.01); *A61M 11/041* (2013.01); *A61M 15/08* (2013.01)

(58) Field of Classification Search
CPC .......... A61M 2021/0016; A61M 21/02; A61M 21/00; A61H 2201/10; A61N 2/002; A61N 2/06; A61N 5/0618
See application file for complete search history.

(56) References Cited

U.S. PATENT DOCUMENTS

| | | | |
|---|---|---|---|
| 2003/0168751 A1* | 9/2003 | Bartsch ............... | A01M 1/2033 261/26 |
| 2009/0082690 A1* | 3/2009 | Phillips .................. | G06Q 50/22 600/544 |
| 2012/0209058 A1* | 8/2012 | Soroush Arasi ..... | A61K 8/0208 600/27 |
| 2013/0137919 A1* | 5/2013 | Pepin ....................... | A61N 2/06 600/28 |

* cited by examiner

*Primary Examiner* — Christine H Matthews
(74) *Attorney, Agent, or Firm* — Guy Levi; The IP Law Firm of Guy Levi, LLC

(57) ABSTRACT

The disclosure relates in general to a device for providing combination aroma and magnetic therapy, as well as mild heating. Specifically, the disclosure relates to a kite-shape device constructed of pure copper with magnets, coupled to a vapor generator for delivering aroma therapy as well as mild heating to a subject in need thereof, fully enclosed therein.

19 Claims, 1 Drawing Sheet

COMBINATION AROMA AND MAGNETOTHERAPY DEVICE AND METHODS OF USE

BACKGROUND

The present disclosure is directed in general to a device for providing synergistic combination of aroma and magnetic therapy. Specifically, the disclosure is directed towards a quadrilateral device constructed of pure metal essential to biochemical processes equipped with magnets, coupled to a vapor generator for delivering aroma therapy.

The poisonous substances and pollutants that are accumulated in the human body include, but are not limited to: pollution poisons, climate poisons, food poisons, agricultural (farm product) chemical poisons, sea pollution poisons (marine products), polluted air and water, electromagnetic waves and stress affecting the human body, poisons due to abuse of medicines and so on. These pollutants damage the blood of the human and cause the destruction of the cells of the human body, and thereby are a major factor in causing diseases such as cancer and diabetes, and other health problems related to blood pressure, the thyroid gland, arthritis, etc.

Copper is an essential trace metals required for many biochemical processes in the body. The brain and liver require the largest amounts of copper and the rest of the organs only a small amount. The body needs approximately 3 mg of copper per day. Most commonly, this amount is not consumed in the modern human diet. However, the redox properties of copper also make the free metal potentially toxic. As a result, uptake and intracellular distribution of copper is tightly regulated. Copper is absorbed from diet across the duodenal brush border membrane by its carrier—Copper transporter 1 (CTR1). This transport step is preceded by the reduction of copper to its cuprous ($Cu^+$) forms, respectively. The nature of the intestinal cupric reductase is assumed to involve DCYTB and STEAP proteins. At the basolateral membrane, ATP7A mediate copper export. In addition, a multi-copper oxidase, hephaestin (HEPH), is required for optimal FPN-mediated iron export, thus linking intestinal copper and iron homeostasis.

In addition, essential oils (EOs) treatments have been used as complimentary treatment that can result to be quite useful.

Likewise, magnetic field based therapy involves the delivery of a particular form of energy to the tissues, much like ultrasound (which happens to be mechanical energy) or laser (which happens to be light based electromagnetic energy). The application of energy to the tissues will result in a physiological change or stimulation, which can in turn be used to generate therapeutic effects.

There is a need for a device that provides controlled targeted aroma therapy with magnetic therapy, while simultaneously increasing the availability of copper ions for absorption by the body.

SUMMARY

In an embodiment, provided herein is a therapeutic device comprising an open, magnetically conductive container having quadrilateral side walls, wherein two disjoint pairs of adjacent walls are equal and wherein a first diagonal is a perpendicular bisector of a second diagonal, and a floor having plurality of apertures defined therein; an upper magnetically conductive lid coupled to the container, adapted to engage the side walls of the container; a first pair of magnets disposed at opposite sides of the first diagonal, the magnets' poles configured to create attractive magnetic force between the magnets; a second pair of magnets disposed at opposite sides of the second diagonal, the magnets' poles configured to create attractive magnetic force between the magnets; and a vapor generator in communication with the floor of the container.

In another embodiment, provided herein is a method of treating a subject in need thereof with a combination aroma and/or magnetic therapy, comprising providing an open, magnetically conductive container having quadrilateral side walls, wherein two disjoint pairs of adjacent walls are equal and wherein a first diagonal is a perpendicular bisector of a second diagonal, and a floor having plurality of apertures defined therein; an upper magnetically conductive lid coupled to the container, adapted to engage the side walls of the container; a first pair of magnets disposed at opposite sides of the first diagonal, the magnets' poles configured to create attractive magnetic force between the magnets; a second pair of magnets disposed at opposite sides of the second diagonal, the magnets' poles configured to create attractive magnetic force between the magnets; and a vapor generator in communication with the floor of the container; placing the subject in the container, wherein the container is configured such that the subject covers between 50% and 75% of the floor's surface area; using the lid, covering the container; generating pulsed magnetic field among the magnets, the magnetic field having a strength of between 5.0 mT and 50 mT; and using the vapor generator, contacting the subject with vapor of a pharmaceutically effective herbal extract.

These and other features of the device for providing combination aroma and magnetic therapy described herein will become apparent from the following detailed description when read in conjunction with the drawings, which are exemplary, not limiting, and wherein like elements are numbered alike in several figures.

BRIEF DESCRIPTION OF THE DRAWINGS

For a better understanding of the device for providing combination aroma and magnetic therapy described herein, with regard to the embodiments thereof, reference is made to the accompanying drawings, in which like numerals designate corresponding elements or sections throughout and in which.

DETAILED DESCRIPTION AS DISCLOSED AND CLAIMED HEREIN

Figure 1:
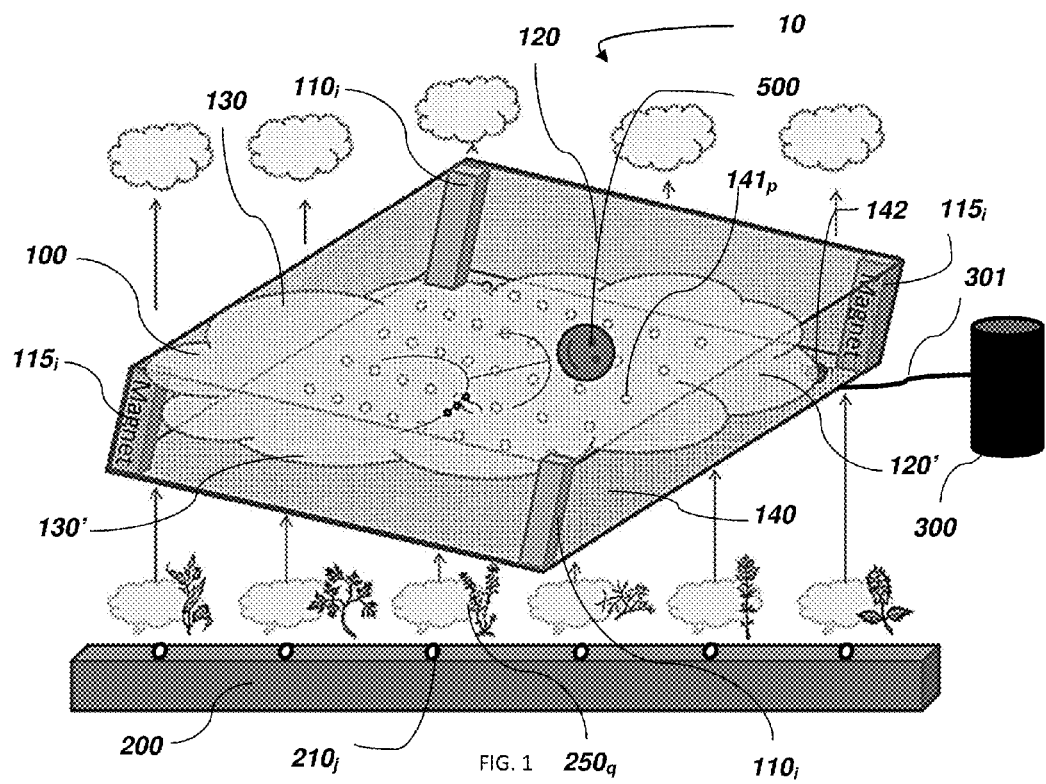
FIG. 1, is view of an embodiment of the device for providing combination aroma and magnetic therapy described herein, illustrating the combination vapor of essential oils, magnetic field therapy as well as mild heat in the treatment of a subject.

Provided herein are embodiments of a device for providing combination aroma and magnetic therapy. More specifically, provided herein are embodiments of a quadrilateral device constructed of pure metal with magnets, coupled to a vapor generator for delivering aroma therapy. In an embodiment, under certain conditions, when 4 magnets are placed into the 4 corners of an enclosed quadrilateral shape of a magnetically conductive metal, e.g., copper, the magnetic field draws the metal containing salts with metal ions out of the magnetically conductive metal and forces the elemental ion to the center of the quadrilateral shape (e.g., a kite shape). When a body is positioned in the center of the device, raised body heat from the aromatherapy vapor can facilitate the contact of the minerals and essential oils (EO's) into the body allowing the body to absorb the metal ions, e.g., copper and the herbs EO's vapor. This process can makes healing processes faster.

In an embodiment, a static magnet, held in proximity to the tissues can bring about bioelectric changes. The magnetic field may be 'static' but the blood moving through the tissues is a conductor, contains ions, and is moving relative to the magnet. Therapy doses can typically range between 0.5-50 milliTesla (mT) (10-1000×'stronger' than the Earth's magnetic field). The field can be pulsed field, for example the amplitude can be 0.5-2.0; 15-20 and 45-50 mT, for a period of between about 3 minutes and 3 hours. The magnetic field generated by the magnets used in the device provided herein can be adapted to selectively generate and deliver static and pulsed magnetic field. The term "selectively" or "selectively generate" refers to circumstances whereby the magnetic field can be activated or deactivated as desired without affecting other components, elements or modules.

Accordingly, provided herein is a therapeutic device comprising an open, magnetically conductive container having quadrilateral side walls, wherein two disjoint pairs of adjacent walls are equal and wherein a first diagonal is a perpendicular bisector of a second diagonal, and a floor having plurality of apertures defined therein; an upper magnetically conductive lid coupled to the container, adapted to engage the side walls of the container; a first pair of magnets disposed at opposite sides of the first diagonal, the magnets' poles configured to create attractive magnetic force between the magnets; a second pair of magnets disposed at opposite sides of the second diagonal, the magnets' poles configured to create attractive magnetic force between the magnets; and a vapor generator in communication with the floor of the container.

The quadrilateral-sided container is characterized in that in certain embodiments, two disjoint pairs of adjacent walls are equal and wherein a first diagonal is a sole perpendicular bisector of a second diagonal, or in other word, a kite shape. In another embodiment, the container is diamond shape. In addition, the container is configured to fully contain the subject, when the lid is lowered or otherwise caused to engage the side walls of the container.

In an embodiment, the term "magnetically conductive" is meant to refer broadly to the ability of a material to conduct magnetic flux. Examples of magnetically conductive materials that could be used include superconductors (which may be ceramic), copper, iron, nickel, cobalt, various alloys, or other materials that exhibit good magnetic permeability. However, other magnetically conductive materials (which may or may not be metal) may also be used without departing from the scope of the technology described herein. For example, the magnetically conductive container and magnetically conductive lid used in the device for providing combination aroma and magnetic therapy described herein can be copper container and copper lid.

The lid used in the device and methods for providing combination aroma and magnetic therapy described herein can be adapted and configured to enclose the container in such a way as not to disrupt the magnetic field center imposed by the magnets. Further, the lid may define a plurality of apertures therein. The apertures can be configured to selectively allow some of the apertures to be blocked, either manually or automatically, thus creating a defined flow pattern of vapor inside the container, when the essential oils (EO's) of herbs are vaporized by the vapor generator. Similarly, the floor of the container, or open box used in the device and methods for providing combination aroma and magnetic therapy described herein can similarly have apertures defined therein, the apertures capable of being selectively blocked or closed to allow control of the flow pattern of the EO's vapor generated by the vapor generator.

The magnets used in the device and methods for providing combination aroma and magnetic therapy described herein can be adapted to provide a controllable center of the magnetic field at any point along the body of the subject. The subject can be fully enclosed within the device. In other words, no part of the subject is outside the closed container. This can be done in an embodiment, by controlling the relative strength of each magnet individually using a central processing unit and a magnetic field generator. The magnetic field generated by the magnet can be a pulsed magnetic field, or a fixed magnetic field and will depend, among other factors, on, for example, the therapeutic indication, the size, age and gender of the subject, whether or not aroma therapy is induced before, simultaneously or after the magnetic therapy or a combination of factors comprising one or more of the foregoing. For example, the first pair of magnets and the second pair of magnets used in the device and methods for providing combination aroma and magnetic therapy described herein can be configured to form a magnetic field having a strength between about 0.5 mT to about 50 mT or between about 1.0 mT and about 45 mT, specifically, between about 5.0 mT and about 40 mT or between about 10 mT and about 35 mT, more specifically, between about 15 mT and about 30 mT, or between about 20 mT and about 30 mT. Pulsing magnetic field can be applied at a frequency of between about 0.01 and 1.0 kHz wherein the pulses can have the same or different strength per pulse. Accordingly, in an embodiment, the field can be fixed and the strength can vary according to a predetermined regimen, or in another example, the pulsed field can have fixed strength per pulse, or a varying strength per pulse.

The duration of the treatment used with the device and methods for providing combination aroma and magnetic therapy described herein can vary greatly, and depend on the same or different factors described above for the strength on character of the magnetic field used. For example, some indications that can be treated using the device and methods for providing combination aroma and magnetic therapy described herein can be; general pain, pain after surgery, low back pain, foot pain, heel pain, osteoarthritis, rheumatoid arthritis, fibromyalgia, chronic fatigue syndrome (CFS), carpel tunnel syndrome, painful menstrual periods, nerve pain caused by diabetes (diabetic neuropathy), sports injuries, migraine headache or a combination comprising one or more of the foregoing nociceptic events. For example, the nociceptic event can be sinus pain, treated by the device disclosed herein with aromatherapy comprising eucalyptus, rosemary lavender, sweet basil, or a combination comprising the foregoing, in combination with focusing the magnetic field above the patient's head, for a therapeutically effective period.

The vapor generator used in the device and methods for providing combination aroma and magnetic therapy described herein can comprise a plurality of vessels operably coupled to a heating source, configured to generate a vapor of a content of the vessel. The term "coupled", including its various forms such as "operably coupling", "coupling" or "couplable", refers to and comprises any direct or indirect, structural coupling, connection or attachment, or adaptation or capability for such a direct or indirect structural or operational coupling, connection or attachment, including integrally formed components and components which are coupled via or through another component or by the forming process. Indirect coupling may involve coupling through an intermediary member or adhesive, or abutting and otherwise resting against, whether frictionally or by separate means without any physical connection.

In an embodiment, the vapor generator can be comprised of various discrete vessels, including a vessel for generating steam. The generator can be located for example below the floor of the container, or be in communication (e.g., material/vapor flow is operatively permitted between enumerated components, directly or indirectly, through a conduit e.g.) with some or all of the plurality of aperture defined in the floor of the container. Moreover, the vapor generator can be configured to increase the heat inside the container, by for example, 2.0° C. to about 15° C.

The aroma therapy used in the device and methods for providing combination aroma and magnetic therapy described herein can involve the use of oils or essences to create a state of mind or mood as well as other therapeutic effects. The essential oils, give off aromas, or essences. Different aromas or essences can affect and/or create particular effects. For example, the aroma of lavender relaxes tension and alleviates stress; the aromas of mint and lemon are considered stimulants. Accordingly, a particular aroma to can be selected to be introduced into the environment, depending on the effect desired. Heating the oils increases in an embodiment, the potency of the aromas. The vapor generator can incorporate a plurality of vessels, in communication with the apertures in the floor of the container, each vessel can contain a discrete EO where the vessel combination may provide the overall needed effect on the subject.

For example, the vapor used in the device and methods for providing combination aroma and magnetic therapy described herein, can be generated from a pharmaceutically effective herbal extract. The herbal extract used in the device and methods for providing combination aroma and magnetic therapy described herein can be the EO of rosemary, eucalyptus, lemon, kava kava, echinacea, St. John's wort, valerian root, milk thistle seed, Siberian ginseng, nettle leaf, ginkgo, gotu kola, ginkgo/gotu kola supreme, astragalus, goldenseal, dong quai, ginseng, St. John's wort supreme, echinacea/goldenseal supreme, bilberry, green tea, hawthorne, ginger, turmeric, black cohosh, cats claw, chamomile, dandelion, chaste tree berry, feverfew, garlic, horse chestnut, licorice, eyebright, yohimbe, astragalus supreme, valerian poppy supreme, or a composition comprising one or more of the foregoing. The vapor can be generated by heating the EO of the herb, or by any other method that would increase the vapor pressure of the EO to the point it will vaporize, for example, by sonication.

The device for providing combination aroma and magnetic therapy described herein can be configured to accommodate a subject such that the subject (which is fully enclosed in the container and lid), will cover between about 50% and 80% of the surface area of the container floor. For example, the sized of the container can be configured not to be too big or too small, as that would decrease the efficiency and effectiveness of the device. In other words, the device used for small children may not be as effective in the treatment of large adults. For example, the first diagonal connecting two joint walls of the quadrilateral shape (e.g., a kite or diamond shapes) is between about 1.5 m and about 2.5 m, while the second diagonal is perpendicular to the first diagonal and is between about 0.7 ml and about 1.5 m. Accordingly, the floor area of the container would vary between about 0.52 $m^2$ and about 1.86 $m^2$. In addition, the side walls of the container can be between 0.5 m and about 1.0 m, for example, 0.7 m.

The container used in the device and methods for providing combination aroma and magnetic therapy described herein, can further comprise a drainage port, making cleaning and removal of condensate easier. In addition, the drainage port can be recessed in the floor of the container, or for example, the floor itself can be configured to drain into a lowest spot where the drainage port can be located.

In an embodiments, the devices described herein, are used in the methods described herein. Accordingly and in another embodiment, provided herein is a method of treating a subject in need thereof with a combination aroma and/or magnetic therapy, comprising: providing an open, magnetically conductive container having quadrilateral side walls, wherein two disjoint pairs of adjacent walls are equal and wherein a first diagonal is a perpendicular bisector of a second diagonal, and a floor having plurality of apertures defined therein; an upper magnetically conductive lid coupled to the container, adapted to engage the side walls of the container; a first pair of magnets disposed at opposite sides of the first diagonal, the magnets' poles configured to create attractive magnetic force between the magnets; a second pair of magnets disposed at opposite sides of the second diagonal, the magnets' poles configured to create attractive magnetic force between the magnets; a lid and a vapor generator in communication with the floor of the container; placing the subject in the container, wherein the container is configured such that the subject covers between 50% and 75% of the floor's surface area; using the lid, covering the container; generating pulsed magnetic field among the magnets, the magnetic field having a strength of between 5.0 mT and 50 mT; and using the vapor generator, contacting the subject with vapor of a pharmaceutically effective herbal extract.

The step of generating pulsed magnetic field operating in the method of treating a subject in need thereof with a combination aroma and/or magnetic therapy, can occur before simultaneously or following the step of contacting the subject with vapor of the pharmaceutically effective herbal extract. Alternatively, the treatment can take place over several courses, with the order changing or remaining the same as needed.

For example, in a given treatment regimen, applying pulsed magnetic field at a strength of between about 10 mT and 30 mT, centered on the gut of the fully enclosed subject can draw the ionized copper salts out of the copper and forces the ions to the center of the field. When the subject is the center of the bed, raised body heat from the steam generated by the vapor generator attracts the minerals and herbs into the body allowing the body to absorb the copper and steamed herbs, thus making healing processes faster.

A more complete understanding of the components, methods, and devices disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof, their relative size relationship and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure.

In the drawings and the following description below, it is to be understood that like numeric designations refer to components of like function. Likewise, cross sections are referred to on normal orthogonal coordinate system having XYZ axis, such that Y axis refers to front-to-back, X axis refers to side-to-side, and Z axis refers to up-and-down.

Figure 2:
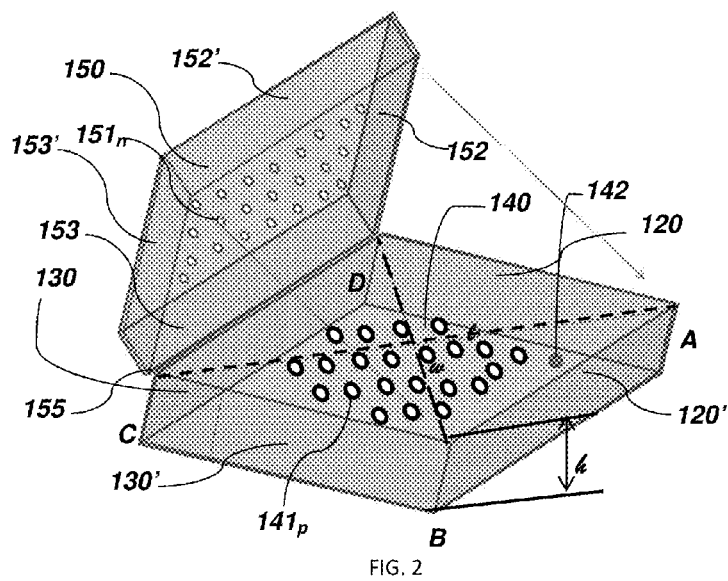
FIG. 2, is an illustration of spatial configuration of the device for providing combination aroma and magnetic therapy.

Turning now to FIGS. 1 and 2, illustrating the combination vapor of essential oils, magnetic field therapy as well as mild heat in the treatment of a subject (FIG. 1) and spatial configuration of the device for providing combination aroma and magnetic therapy (FIG. 2). As shown, therapeutic device 10 for delivering synergistic and complementary combination of aroma and magnetic therapy to subject 500 in need thereof, device 10 comprising open, magnetically conductive container 100 (e.g., copper) having quadrilateral side walls, wherein two disjoint pairs (120, 120', 130, 130', respectively) of adjacent walls are equal and wherein first diagonal AC, FIG. 2 is a perpendicular bisector of second diagonal BD, FIG. 2, and floor 140 having plurality of apertures $141_p$ defined therein and drainage port 142 that can be recessed in floor 140, allowing for removal of steam condensate or other vapor condensate and cleaning of container 100.

As shown in FIG. 2, device 10 can comprise upper magnetically conductive lid 150, for example, copper or aluminum, coupled to container 100, adapted to engage side walls 120, 120', 130, 130' of container 100. The term "engage" and various forms thereof, when used with reference to retention of lid 150, refer to the application of any forces that tend to hold lid 150 and container 100 together against inadvertent or undesired separating forces (e.g., such as may be introduced during use of device 10). It is to be understood, however, that engagement does not in all cases require an interlocking connection that is maintained against every conceivable type or magnitude of separating force. Container lid 150 van further define selectively and reversibly closeable apertures $151_n$. Lid 150 can have side walls 152, 152' and 153, 153' configured to engage quadrilateral side walls 120, 120' and 130, 130' respectively, creating full enclosure of subject 500 (FIG. 1) by device 10.

Also shown in FIG. 1, is first pair of magnets $115_i$ disposed at opposite sides of first diagonal AC (FIG. 2), magnets' $115_i$ poles configured to create attractive magnetic force between the magnets with second pair of magnets $110_i$ disposed at opposite sides of second diagonal BD (FIG. 2), $110_i$ magnets' poles configured to create attractive magnetic force between the magnets. Also shown in FIG. 1, is vapor generator 200 in communication with floor 140 of container 100. As shown, Vapor generator 200 can define various discrete openings or apertures $210_j$, configured to communicate with some or all apertures $141_p$ defined in floor 140 of container 100, made in an embodiment of pure copper. Magnets $110_i$, $115_i$, can be each and or all be controlled by field generator 300 operably coupled to container 100 through conduit 301 (see FIG. 1). Field generator 300 and vapor generator 200 can be operably coupled to a central processing unit (not shown), configured to control magnets $110_i$, $115_i$, strength, pulse(s), field and/or treatment duration or a combination of factors comprising one or more of the foregoing; as well as type of aroma, duration of each vaporization, temperature control, which if any of apertures $141_p$ and $151_n$ shall be opened or closed and the like or a combination comprising one or more of the foregoing. Accordingly, device 10 can be equipped with various sensors (not shown), for example, temperature sensors, pH sensors, heart rate sensors, blood pressure sensors, microphone(s), camera(s) or sensor combination comprising one or more of the foregoing.

Turning now to FIG. 2, illustrating an embodiment of the quadrilateral shape of container 10, illustrated in a diamond shape. In another embodiment, the shape of device 10 is a kite shape where only diagonal AC bisects diagonal AD. As shown, diagonal AC is designated the identifier "l", while diagonal BD is designated the identifier "w", while the height of side walls 120, 120', 130, 130' is designated the identifier "h". In an embodiment, l can be between about 1.5 m and about 2.5 m, while w can be between about 0.7 m and about 1.5 m, while h can be between about 0.5 m and about 1.0 m.

The term "about", when used in the description of the technology and/or claims means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such and may include the end points of any range provided including, for example ±25%, or ±20%, specifically, ±15%, or ±10%, more specifically, ±5% of the indicated value of the disclosed amounts, sizes, formulations, parameters, and other quantities and characteristics.

All ranges disclosed herein are inclusive of the endpoints, and the endpoints are independently combinable with each other. "Combination" is inclusive of blends, mixtures, alloys, reaction products, and the like. Furthermore, the terms "first," "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the pulse(s) includes one or more pulses). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended, are intended to embrace all such alternatives, modifications variations, improvements, and substantial equivalents.

What is claimed:

1. A therapeutic device comprising:
   a. an open, magnetically conductive container having quadrilateral side walls, wherein two disjoint pairs of adjacent walls are equal and wherein a first diagonal of the open, magnetically conductive container having quadrilateral side walls is a perpendicular bisector of a second diagonal of the open, magnetically conductive container having quadrilateral side walls and is longer than the second diagonal of the open, magnetically conductive container having quadrilateral side walls, and a floor having a plurality of apertures defined therein;

b. an upper magnetically conductive lid coupled to the container, adapted to engage the side walls of the container;

c. a first pair of magnets disposed at opposite sides of the first diagonal of the open, magnetically conductive container having quadrilateral side walls, the first pair of magnets' poles configured to create attractive magnetic force between the first pair of magnets;

d. a second pair of magnets disposed at opposite sides of the second diagonal of the open, magnetically conductive container having quadrilateral side walls, the second pair of magnets' poles configured to create attractive magnetic force between the second pair of magnets; and e. a vapor generator in communication with the floor of the container.

2. The device of claim 1, wherein the open, magnetically conductive container and the magnetically conductive lid coupled thereto are a copper container and a copper lid.

3. The device of claim 1, wherein the magnetically conductive lid further defines a plurality of apertures therein.

4. The device of claim 1, wherein the apertures defined in the floor of the container are adapted to be selectively blocked.

5. The device of claim 3, wherein the apertures defined in the lid are adapted to be selectively blocked.

6. The device of claim 1, wherein the first pair of magnets and the second pair of magnets are configured to form a magnetic field having a strength between about 5.0 mT to about 50 mT.

7. The device of claim 6, wherein the first pair of magnets and the second pair of magnets are configured to form a magnetic field having a strength between about 10 mT to about 30 mT.

8. The device of claim 1, wherein the vapor generator comprises a plurality of vessels coupled to a heating source, configured to generate a vapor of a content of each of the vessels.

9. The device of claim 8, wherein the vapor is generated from a pharmaceutically effective herbal extract.

10. The device of claim 9, wherein the herbal extract is of rosemary, eucalyptus, lemon, kava kava, echinacea, St. John's wort, valerian root, milk thistle seed, Siberian ginseng, nettle leaf, ginkgo, gotu kola, ginkgo/gotu kola supreme, astragalus, goldenseal, dong quai, ginseng, St. John's wort supreme, echinacea/goldenseal supreme, bilberry, green tea, hawthorne, ginger, turmeric, black cohosh, cats claw, chamomile, dandelion, chaste tree berry, feverfew, garlic, horse chestnut, licorice, eyebright, yohimbe, astragalus supreme, valerian poppy supreme, or a composition comprising one or more of the foregoing.

11. The device of claim 1, wherein the first diagonal of the open, magnetically conductive container having quadrilateral side walls is between about 1.5 m and about 2.5 m.

12. The device of claim 11, wherein the second diagonal of the open, magnetically conductive container having quadrilateral side walls is perpendicular to the first diagonal and is between about 0.7 m and about 1.5 m.

13. The device of claim 12, wherein a height of the quadrilateral side walls are between 0.5 m and about 1.0 m.

14. The device of claim 1, wherein the vapor generator is located below the floor.

15. The device of claim 1, wherein the container further comprises a drainage port.

16. The device of claim 1, wherein the magnets generate a pulsed magnetic field.

17. A method of treating a subject in need thereof with a combination aroma and magnetic therapy, comprising:

a. providing an open, magnetically conductive container having quadrilateral side walls, wherein two disjoint pairs of adjacent walls are equal and wherein a first diagonal of the open, magnetically conductive container having quadrilateral side walls is a perpendicular bisector of a second diagonal of the open, magnetically conductive container having quadrilateral side walls, and a floor having a plurality of apertures defined therein; an upper magnetically conductive lid coupled to the container, adapted to engage the side walls of the container; a first pair of magnets disposed at opposite sides of the first diagonal of the open, magnetically conductive container having quadrilateral side walls, the first pair of magnets' poles configured to create attractive magnetic force between the first pair of magnets; a second pair of magnets disposed at opposite sides of the second diagonal of the open, magnetically conductive container having quadrilateral side walls, the second pair of magnets' poles configured to create attractive magnetic force between the second pair of magnets; and a vapor generator in communication with the floor of the container;

b. enclosing the subject in the container, wherein the container is configured such that the subject covers between 50% and 75% of the floor's surface area; using the upper magnetically conductive lid, covering the container;

c. generating a pulsed magnetic field among the magnets, the magnetic field having a strength of between 5.0 mT and 50 mT; and d. using the vapor generator, contacting the subject with vapor of a pharmaceutically effective herbal extract.

18. The method of claim 17, wherein the step of generating the pulsed magnetic field occurs simultaneously or following the step of contacting the subject with vapor of the pharmaceutically effective herbal extract.

19. The method of claim 17, further comprising increasing the temperature within the container by between about 2° C. and about 15° C.

* * * * *